United States Patent
Cho et al.

(10) Patent No.: US 11,337,678 B2
(45) Date of Patent: *May 24, 2022

(54) ULTRASOUND PROBE AND METHOD OF OPERATING THE SAME

(71) Applicant: Samsung Electronics Co., Ltd., Gyeonggi-do (KR)

(72) Inventors: Jeong Cho, Seoul (KR); Se-tae Kim, Seoul (KR); Ho-san Han, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 998 days.

This patent is subject to a terminal disclaimer.

(21) Appl. No.: 15/888,258

(22) Filed: Feb. 5, 2018

(65) Prior Publication Data

US 2018/0153519 A1 Jun. 7, 2018

Related U.S. Application Data

(63) Continuation of application No. 14/476,006, filed on Sep. 3, 2014, now Pat. No. 9,901,324.

(30) Foreign Application Priority Data

Sep. 3, 2013 (KR) .......................... 10-2013-0105698

(51) Int. Cl.
  *A61B 8/08* (2006.01)
  *G01S 7/52* (2006.01)
  *A61B 8/00* (2006.01)

(52) U.S. Cl.
  CPC .......... *A61B 8/5207* (2013.01); *A61B 8/4411* (2013.01); *A61B 8/4438* (2013.01);
  (Continued)

(58) Field of Classification Search
  CPC ....... A61B 8/00; A61B 8/4438; A61B 8/4444; A61B 8/4472; A61B 8/54; A61B 8/56
  See application file for complete search history.

(56) References Cited

U.S. PATENT DOCUMENTS 6,780,154 B2    8/2004  Hunt et al.
8,702,611 B2 *  4/2014  Ohshima ................ A61B 8/467
                                                    600/447

(Continued)

FOREIGN PATENT DOCUMENTS

JP    2000-325350 A    11/2000
JP    2007-275087 A    10/2007

(Continued)

OTHER PUBLICATIONS

Korean Search Report dated Dec. 3, 2020.
Korean Notice of Allowance dated Jun. 22, 2021.

*Primary Examiner* — Baisakhi Roy
(74) *Attorney, Agent, or Firm* — Cha & Reiter, LLC

(57) ABSTRACT

An ultrasound probe connected to various diagnostic apparatuses and a method of operating the ultrasound probe. The includes transmitting an ultrasound signal to an object and receiving a response signal reflected from the object; acquiring information regarding a diagnostic apparatus connected to the ultrasound probe; determining a type of data that may be processed by the diagnostic apparatus based on the information regarding the diagnostic apparatus; generating transmission data corresponding to the determined type of data from the response signal; and transmitting the transmission data to the diagnostic apparatus.

14 Claims, 7 Drawing Sheets

(52) U.S. Cl.
CPC .......... *A61B 8/4444* (2013.01); *A61B 8/4472* (2013.01); *A61B 8/54* (2013.01); *A61B 8/56* (2013.01); *G01S 7/5208* (2013.01); *G01S 7/52082* (2013.01); *A61B 8/4405* (2013.01); *A61B 8/4427* (2013.01)

(56) References Cited

U.S. PATENT DOCUMENTS

| | | | |
|---|---|---|---|
| 8,721,551 B2* | 5/2014 | Tanabe | A61B 8/4477 |
| | | | 600/459 |
| 9,218,452 B2* | 12/2015 | Varna | A61B 8/585 |
| 9,622,718 B2 | 4/2017 | Watanabe | |
| 9,901,324 B2* | 2/2018 | Cho | A61B 8/5207 |
| 2008/0255451 A1 | 10/2008 | Cohen et al. | |
| 2010/0168576 A1 | 7/2010 | Poland et al. | |
| 2010/0191121 A1* | 7/2010 | Satoh | A61B 8/56 |
| | | | 600/459 |
| 2011/0077522 A1* | 3/2011 | Sato | A61B 8/4472 |
| | | | 600/447 |
| 2012/0071762 A1* | 3/2012 | Sato | A61B 8/4444 |
| | | | 600/459 |
| 2013/0028153 A1 | 1/2013 | Kim et al. | |
| 2013/0253327 A1 | 9/2013 | Ko et al. | |
| 2014/0171802 A1* | 6/2014 | Kuroiwa | A61B 8/4411 |
| | | | 600/459 |
| 2014/0236010 A1* | 8/2014 | Nakano | A61B 8/463 |
| | | | 600/440 |

FOREIGN PATENT DOCUMENTS

| | | |
|---|---|---|
| JP | 2010-528696 A | 8/2010 |
| JP | 2012-090712 A | 5/2012 |
| JP | 2012-139491 A | 7/2012 |
| KR | 10-2010-0057341 A | 5/2010 |
| KR | 10-2012-0055763 A | 6/2012 |
| KR | 10-2012-0124123 A | 11/2012 |
| KR | 10-2013-0012501 A | 2/2013 |
| WO | 2010/122791 A1 | 10/2010 |

* cited by examiner

ULTRASOUND PROBE AND METHOD OF OPERATING THE SAME

CROSS REFERENCE TO RELATED APPLICATIONS

This application is a Continuation of U.S. patent application Ser. No. 14/476,006 filed on Sep. 3, 2014 which claims the benefit of Korean Patent Application No. 10-2013-0105698, filed on Sep. 3, 2013, in the Korean Intellectual Property Office, the disclosure of which is incorporated herein in its entirety by reference.

BACKGROUND

1. Field

One or more embodiments of the present invention relate to an ultrasound probe and a method of operating the ultrasound probe, and more particularly, to an ultrasound probe connected to various diagnostic apparatuses and a method of operating the ultrasound probe.

2. Description of the Related Art

Ultrasound systems irradiate an ultrasonic signal generated from a transducer of an ultrasound probe onto an internal part of an object and receive information of an echo signal reflected from the internal part of the object, thereby acquiring an image of the internal part of the object. In particular, ultrasound systems are used for the medical purpose of observing the inside of an object, detecting a foreign material, assessing internal injuries, imaging fetuses and the like.

Ultrasound systems have stabilities higher than those of diagnostic apparatuses using X-rays, display an image in real time, and are safe because there is no exposure to radioactivity, and thus may be widely used on their own and/or along with other medical image diagnostic apparatuses.

It may be inconvenient for a user to acquire an ultrasound image of an object by using an ultrasound probe due to a communication cable used to connect the ultrasound probe and a diagnostic apparatus. Further, the communication cable poses challenges for manufacturers of the probes and of the diagnostic apparatuses, as the real and imaginary impedances of the cable and the connectors of diagnostic apparatuses must be matched very carefully, in order to avoid noise levels and the like, which may affect the resulting image quality to be displayed by or on the diagnostic apparatuses, in particular in embodiments where signal processing to generate image data is achieved in the diagnostic apparatuses and the response signal is transmitted from the probe to the diagnostic apparatus.

To improve operability of the ultrasound probe by removing the cable and/or the inconveniences caused by the communication cable, there may be a need for a wireless ultrasound probe that is connected to an ultrasound diagnostic apparatus by wireless communication.

Moreover, when a wireless (or wired) ultrasound probe is subordinate to one ultrasound diagnostic apparatus, since each of a plurality of ultrasound diagnostic apparatuses needs to include a plurality of wireless ultrasound probes, there are problems in that manufacturing costs are high and management is difficult.

Different probes and/or types of probes, which are all subordinate to one particular diagnostic apparatus, cannot be employed with any other diagnostic apparatus. Consequently, for each diagnostic apparatus, the hospital or other facility needs to acquire a full range of probes for each diagnostic apparatus, which increases costs. In relation to management it is noted, that, for instance, an operator must be aware precisely to which diagnostic apparatus a chosen probe for examination of a particular object belongs. Otherwise, communication problems will occur and medical imaging may turn out not to be possible, and a person as the object under examination will be caused concerns and possibly even anxiety, when the medical equipment does not immediately appear to be functioning properly, when initiating the examination. Thus, there is a need for an ultrasound probe, for instance a wireless ultrasound probe, that is not subordinate to one ultrasound diagnostic apparatus but may communicate with a plurality of ultrasound diagnostic apparatuses.

Based in these considerations, the inventive concept of the present disclosure may be equally applicable in embodiments of probes employing wired communication connections with diagnostic apparatuses, for instance when signal processing is performed in the probes.

SUMMARY

One or more embodiments of the present invention include an ultrasound probe which is connectable to various diagnostic apparatuses and a method of operating the ultrasound probe.

One or more embodiments of the present invention include an ultrasound probe for generating transmission data that may be processed by a diagnostic apparatus connected to the ultrasound probe based on information regarding the diagnostic apparatus and transmitting the transmission data to the diagnostic apparatus by using a communication method and/or a transmission signal format used by the diagnostic apparatus, and a method of operating the ultrasound probe. Connection between the diagnostic apparatus and the probe, and communications between the probe and the diagnostic apparatus may be wired or wireless.

Additional aspects will be set forth in part in the description which follows and, in part, will be apparent from the description, or may be learned by practice of the presented embodiments.

According to one or more embodiments of the present invention, there is provided a method of operating an ultrasound probe, the method comprising: transmitting an ultrasound signal to an object and receiving a response signal reflected from the object; determining at least one type of data that a diagnostic apparatus is arranged to process, which diagnostic apparatus is connected to the ultrasound probe, from a plurality of various diagnostic apparatuses, which are connectable to the ultrasound probe; generating transmission data from the response signal in correspondence to the determined type of data; and transmitting the transmission data to the diagnostic apparatus. It is noted in this respect that the steps of the method are not necessarily sequentially presented above and defined in the appended claims. For instance, the step of determining a type of data for the connected diagnostic apparatus may precede the step of transmitting the ultrasound signal and receiving the response or echo signal back from (the interior) of the object. Types of data for a range of various diagnostic apparatuses may even be stored in the probe, even before any transmission of ultrasound signals and/or reception of response signals is performed. Embodiments of the present disclosure having these features exhibit the advantage without these features that the cooperation between a single probe and a plurality of various types of diagnostic apparatuses is made possible, and vice versa.

The determining of the at least one type of data that the connected diagnostic apparatus is arranged to process, may comprise: acquiring at least one of: a type of data, which the diagnostic apparatus is arranged to process, a wireless communication method used by the diagnostic apparatus, a wired communication method used by the diagnostic apparatus, and an identifier of the diagnostic apparatus. Embodiments in this aspect of the present disclosure having these features exhibit the advantage or benefit over embodiments without these features without such features that initialisation of the communication between the probe and the diagnostic apparatus may immediately yield improved cooperation, and allow plural diagnostic apparatuses and probe to cooperate using different communication methods and possibly using storage and/or mapping of the suitable types transmission data to which a probe may be connected beforehand.

The method may further include, after acquiring the identifier of the diagnostic apparatus: storing the identifier of each of the plurality of various diagnostic apparatuses, that are connectable to the ultrasound probe, and mapping the stored identifiers onto at least one of: at least one type of data that each of the plurality of diagnostic apparatuses, that is associated with the identifier, is arranged to process; and a wired or wireless communication method used by each of the plurality of diagnostic apparatuses. Embodiments in this aspect of the present disclosure having these features exhibit the advantage or benefit over embodiments without these features that a match between the suitable type of transmission data and the one type of various diagnostic apparatuses may be pre-stored, after which only an ID of the diagnostic apparatus is required to be obtained, to thereafter adapt the probe and the manner of functioning thereof to the type of an actually connected diagnostic apparatus.

The method may further include that the generating of the transmission data comprises using at least one image processing unit of the ultrasound probe for processing the response signal to generate the transmission data from the response signal in correspondence with at least one type of data that the connected diagnostic apparatus is arranged to process.

The ultrasound probe may include at least one image processing unit for processing the response signal in at least two subsequent signal and/or image processing steps at least towards generating an image, wherein the generating of the transmission data may include: selecting a number of subsequent signal and/or image processing steps for processing of the response signal, necessary for generating the transmission data corresponding to the determined type of data; and generating the transmission data by using the selected signal and/or image processing steps. Embodiments in this aspect of the present disclosure having these features exhibit the advantage or benefit over embodiments without these features that of all the subsequent steps to process the response signal to obtaining ultrasound images, some may be performed in or by the probe, and some may be performed in or by the diagnostic connected apparatus. Such complementary cooperation between probes and diagnostic apparatuses is elegant allows tailor made cooperation between the probe and the diagnostic apparatus, based on essentially the capabilities of the actually connected diagnostic apparatus to promote processing of subsequent signal and/or image processing steps further towards obtaining an ultrasound image, thereby relieving load of and/or power consumption by the probe. Further, such diagnostic apparatuses may exhibit improved shielding or more powerful processors, in comparison with the relatively small size probes, to allow probes to generate ultrasound images or enable the probes to stop processing at some stage intermediate between the response signal and furnishing the ultrasound images and leaving as many steps in these subsequent processing steps as possible to the diagnostic device, adding to the versatility of the thus obtained cooperation between the probe and the actually connected diagnostic apparatus.

The generating of the transmission data may include: preventing the at least one signal and/or image processing unit from performing any other steps than the selected number of signal and/or image processing steps. Embodiments in this aspect of the present disclosure having these features exhibit the advantage or benefit over embodiments without these features of a reduction of power consumption of several processors which may be powered down. A single processor may be prevented from having to perform all steps to arrive at the ultrasound image, thus reducing load of and power consumption by such a single processor. The at least one processor may process signals or images.

The transmitting of the transmission data may include: determining a communication method used by the diagnostic apparatus based on the determined type of data that the diagnostic apparatus is arranged to process; and transmitting the transmission data by using the determined communication method. Embodiments in this aspect of the present disclosure having these features exhibit the advantage or benefit over embodiments without these features that unselected communication units may be powered down, adding to power savings.

The determining of the wireless communication method used by the diagnostic apparatus may include: determining at least one of wireless LAN, Wi-Fi, Bluetooth, Zigbee, Wi-Fi Direct (WFD), UWB, infrared data association (IrDA), Bluetooth low energy (BLE), near field communication (NFC), wireless broadband Internet (Wibro), world interoperability for microwave access (WiMAX), shared wireless access protocol (SWAP), wireless gigabit allicance (WiGig), and radio frequency (RF) communication as the wireless communication method used by the diagnostic apparatus.

The transmitting of the transmission data may comprise using at least one communication unit of the ultrasound probe for transmitting the transmission data by using at least one of different communication methods in correspondence with the at least one type of data that the various diagnostic apparatuses, which are connectable to the ultrasound probe, are arranged to process.

The ultrasound probe may include a plurality of communication units for transmitting the transmission data, for instance by using different wireless communication methods, wherein the transmitting of the transmission data comprises: selecting at least one communication unit corresponding to the communication method used by the diagnostic apparatus from the plurality of communication units corresponding to the determined type of data, that the diagnostic apparatus is arranged to process.

The transmitting of the transmission data may include: determining a first communication method and a second communication method that are used by the diagnostic apparatus based on the determined type of data that the diagnostic apparatus is arranged to process; selecting a first communication unit corresponding to the first communication method and a second communication unit corresponding to the second communication method from the plurality of communication units; and transmitting the transmission data by using the first communication unit and optionally transmitting and/or receiving at least one of state information data of the ultrasound probe and control data of the diagnostic apparatus by using the second communication unit. Embodiments in this aspect of the present disclosure having these features exhibit the advantage or benefit over embodiments without these features that communications flows can be generated using the different communication units, thereby optimizing the total transfers, without interference or interruption.

According to one or more embodiments of the present invention, there is provided an ultrasound probe including: an ultrasound transceiving unit for transmitting an ultrasound signal to or into an object and receiving a response signal reflected from the object or from within the object; a control unit for determining at least one type of data that a diagnostic apparatus is arranged to process, which diagnostic apparatus is in use connected to the ultrasound probe, from a plurality of various diagnostic apparatuses, which are connectable to the ultrasound probe; a transmission data generating unit for generating transmission data from the response data in correspondence with the determined type of data; and a communication unit for transmitting the transmission data to the diagnostic apparatus.

The control unit may determine at least one type of data that the connected diagnostic apparatus is arranged to process, by acquiring at least one of: a type of data which the diagnostic apparatus is arranged to process; a wireless communication method used by the diagnostic apparatus, a wired communication method used by the diagnostic apparatus; and an identifier of the diagnostic apparatus.

The ultrasound probe wherein the control unit acquires the identifier of the diagnostic apparatus, may further include: a storage unit for storing the identifier of each of the plurality of various diagnostic apparatuses that are connectable to the ultrasound probe, and mapping the stored identifiers onto at least one of: at least one type of data that each of the plurality of various diagnostic apparatuses that is associated with the identifier, is arranged to process; and a wired or wireless communication method used by each of the plurality of diagnostic apparatuses.

The transmission data generating unit may include at least one image processing unit for processing the response signal to generate the transmission data from the response signal in correspondence with at least one type of data that the various diagnostic apparatuses, which are connectable to the ultrasound probe, are arranged to process, and wherein, when the transmission data generating unit comprises a plurality of image processing units for processing the response signal, the control unit controls the transmission data generating unit to select at least one of the plurality of image processing units necessary for generating the transmission data corresponding to the determined type of data, and generate the transmission data by using the selected at least one image processing unit.

The control unit may disable the image processing units excluding the selected at least one image processing unit.

The control unit may control the communication unit to determine a communication method used by the diagnostic apparatus based on the determined type of data that the diagnostic apparatus is arranged to process, and transmit the transmission data by using the determined communication method.

The control unit may determine at least one of wireless LAN, Wi-Fi, Bluetooth, Zigbee, WFD, UWB, IrDA, BLE, NFC, Wibro, WiMAX, SWAP, WiGig, and RF communication as the wireless communication method used by the diagnostic apparatus.

The ultrasound probe may include a plurality of communication units for transmitting the transmission data by using different communication methods, wherein the control unit selects at least one communication unit corresponding to the communication method used by the diagnostic apparatus from the plurality of communication units based on the type of data, which the diagnostic apparatus is arranged to process, and controls the selected at least one communication unit to transmit the transmission data.

The control unit may determine a first communication method and a second communication method that are used by the diagnostic apparatus based on the determined type of data, which the diagnostic apparatus is arranged to process, selects a first communication unit corresponding to the first wireless communication method and a second communication unit corresponding to the second wireless communication method from the plurality of communication units, controls the first communication unit to transmit the transmission data to the diagnostic apparatus and controls the second communication unit to transmit and/or receive at least one of state information data of the ultrasound probe and control data of the diagnostic apparatus to the diagnostic apparatus.

According to one or more embodiments of the present invention, there is provided a computer-readable storage medium storing a computer program for executing the method of operating an ultrasound probe, the method including: transmitting an ultrasound signal to an object and receiving a response signal reflected from the object; determining at least one type of data that a diagnostic apparatus is arranged to process, which diagnostic apparatus is connected to the ultrasound probe, from a plurality of various diagnostic apparatuses, which are connectable to the ultrasound probe; generating transmission data from the response signal in correspondence to the determined type of data; and transmitting the transmission data to the diagnostic apparatus.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
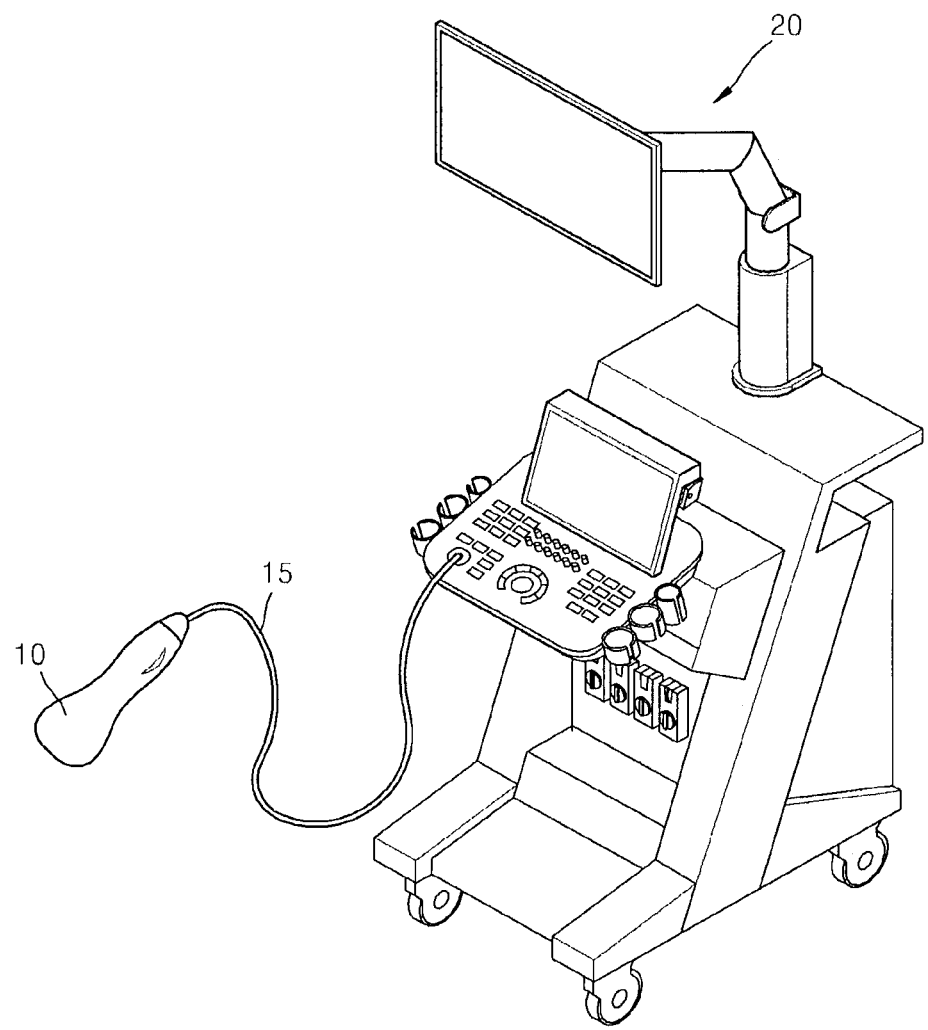
FIG. 1 is a diagram of a general ultrasound apparatus according to a wired embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present disclosure.

Throughout the specification, when an element is referred to as being "connected" or "coupled" to another element, it may be "directly connected or coupled" to the other element, and/or may be "electrically connected or coupled" with intervening elements, and/or may be wired or wirelessly in communication with the another element.

When a part "includes" or "comprises" an element, unless there is a particular description contrary thereto, the part may further include other elements, not excluding the other elements.

Moreover, each of terms such as " . . . unit" and "module" described in specification denotes an element for performing at least one function or operation, and may be implemented in hardware, software or a combination of hardware and software.

The term "ultrasonic image" used herein denotes an image of an object acquired by using an ultrasonic wave. Also, the term "object" used herein may be an organic substance or an inorganic substance indicated by the image. The object may include a part of a physical body. For example, an object may include an organ such as a liver, a heart, a womb, a brain, breasts, an abdomen, or the like, or a fetus, and may include a cross-sectional surface of the physical body.

Moreover, the term "user" used herein is a medical expert, and may be a doctor, a nurse, a medical technologist, a sonographer, a medical image expert, or the like. However, the user is not limited thereto.

Aspects and details of the present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. In the following description, well-known functions or constructions are not described in detail since they would obscure the invention with unnecessary detail. As used herein, the term "and/or" includes any and all combinations of one or more of the associated listed items. Expressions such as "at least one of," when preceding a list of elements, modify the entire list of elements and do not modify the individual elements of the list.

FIG. 1 is a diagram of a general ultrasound apparatus according to a wired embodiment of the present invention.

Referring to FIG. 1, the general ultrasound apparatus includes an ultrasound probe 10 and a diagnostic apparatus 20 connected to the ultrasound probe 10 via a communication cable 15.

The ultrasound probe 10 transmits an ultrasound signal to or into an object according to a control signal transmitted from the diagnostic apparatus 20, receives a response signal (or an ultrasound echo signal) reflected from the object, and forms a receiving signal. The ultrasound probe 10 focuses the ultrasound signal, forms ultrasound image data from the receiving signal, and transmits the ultrasound image data to the diagnostic apparatus 20.

The diagnostic apparatus 20 may form and display an ultrasound image by using the ultrasound image data transmitted from the ultrasound probe 10.

As indicated above, there is a need for a preferably wireless ultrasound probe that is not subordinate to one ultrasound diagnostic apparatus but may communicate with a plurality of ultrasound diagnostic apparatuses. However, a type of data transmitted from the ultrasound probe 10 to the diagnostic apparatus 20 and a preferably wireless communication method used to transmit the data are fixed for any combination of a probe and the diagnostic apparatus to which the probe belongs or is sub-ordinate to. Thus, a diagnostic apparatus that may be connected to one ultrasound probe is very limited.

One or more embodiments of the present invention provide an ultrasound probe that may be connected to various diagnostic apparatuses by selectively outputting an appropriate type of data according to a characteristic of a diagnostic apparatus connected to the ultrasound probe.

Figure 2:
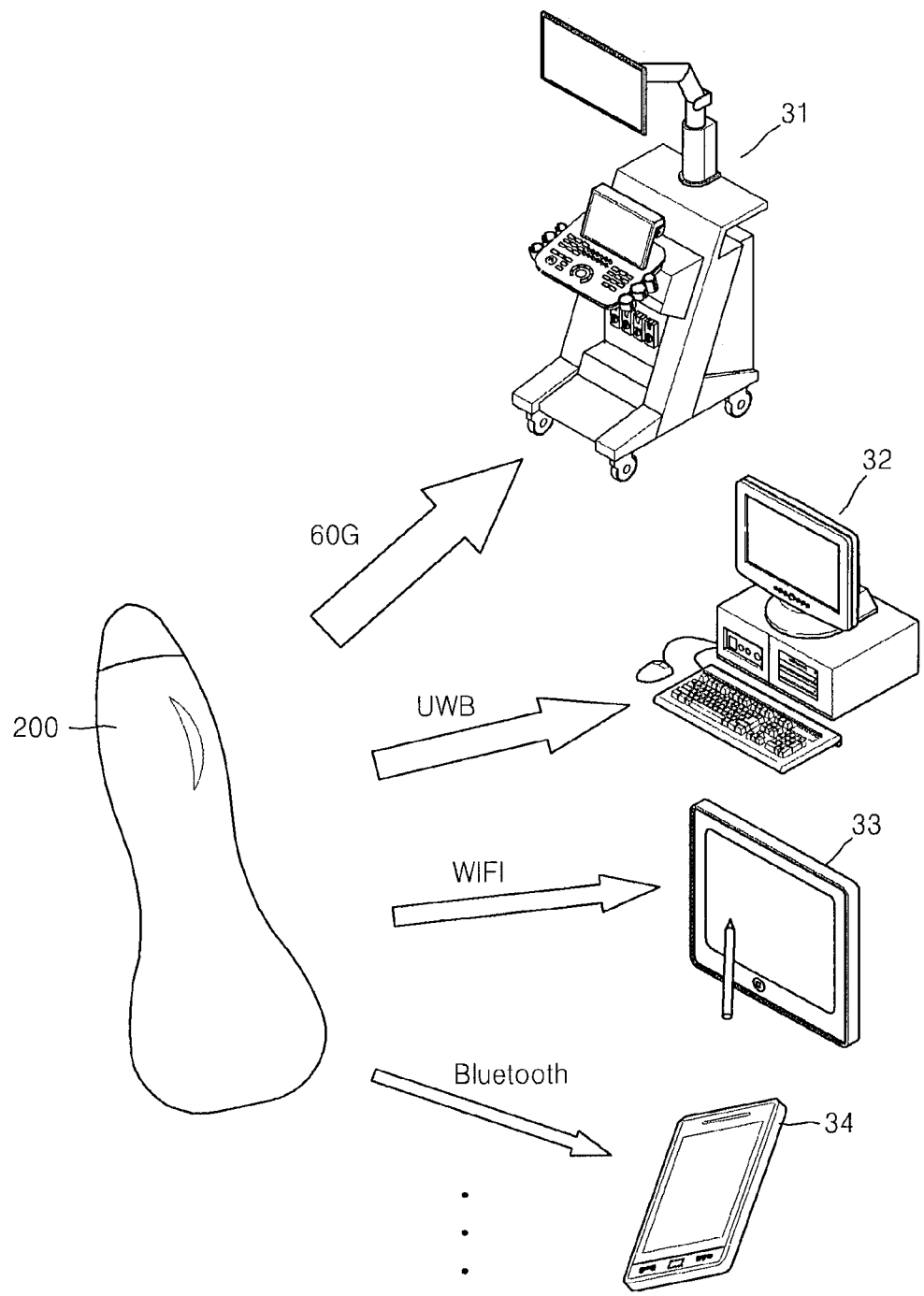
FIG. 2 is a conceptual diagram for explaining an ultrasound system including an ultrasound probe according to an embodiment of the present invention.

FIG. 2 is a conceptual diagram for explaining an ultrasound system including an ultrasound probe 200 according to an embodiment of the present invention.

Referring to FIG. 2, the ultrasound probe 200 according to an embodiment of the present invention may be used by being connected to a plurality of diagnostic apparatuses 31, 32, 33, and 34 having various characteristics. The probe may be connected through wires or cables with any one of the diagnostic apparatuses 31-34, or wirelessly.

In this regard, a "diagnostic apparatus" is an apparatus that is connected to the ultrasound probe 200 by wire or wirelessly and provides a user with an ultrasound image by using ultrasound image data received from the ultrasound probe 200.

In this regard, each of the plurality of diagnostic apparatuses 31, 32, 33, and 34 may be connected together or alone to the ultrasound probe 200 and provide a user with an ultrasound image by using ultrasound image data received from the ultrasound probe 200.

Each of the plurality of diagnostic apparatuses 31, 32, 33, and 34 may be configured as a cart type diagnostic apparatus as well as a portable diagnostic apparatus. The portable diagnostic apparatus may include a picture archiving and communication system (PACS) viewer, a hand-carried cardiac ultrasound (HCU) device, a smart phone, a lap-top computer, a personal digital assistant (PDA), and a tablet personal computer (PC), but is not limited thereto.

Each of the plurality of diagnostic apparatuses 31, 32, 33, and 34 that may be connected to the ultrasound probe 200 according to an embodiment of the present invention may process ultrasound image data received from the ultrasound probe 200, generate an ultrasound image, and display the ultrasound image, or may perform only an image display function without having an image processing function. That is, each of the plurality of diagnostic apparatuses 31, 32, 33, and 34 may include a display apparatus that receives an image from the ultrasound probe 200 and displays the image on a screen without performing additional processing on the image.

For example, as shown in FIG. 2, the diagnostic apparatuses 31, 32, 33, and 34 that may be connected to the ultrasound probe 200 may be a cart type ultrasound diagnostic apparatus 31, a PC 32, a PDA 33, and a smart phone 34. The diagnostic apparatuses 31, 32, 33, and 34 of FIG. 2 process different types of ultrasound image data, and or may process the same ultrasound image data differently and/or may have different functionalities and/or performances.

The diagnostic apparatuses 31, 32, 33, and 34 may use different wireless communication methods. As shown in FIG. 2, wireless communication methods used by the diagnostic apparatuses 31, 32, 33, and 34 may include 60G, ultra wide band (UWB), WiFi, and Bluetooth.

One or more embodiments of the present invention may provide the ultrasound probe 200 that may be used by being connected to the diagnostic apparatuses 31, 32, 33, and 34 having various characteristics and a method of operating the ultrasound probe 200.

Therefore, the ultrasound probe 200 according to an embodiment of the present invention may output different types of ultrasound image data according to the diagnostic apparatuses 31, 32, 33, and 34 and in correspondence with a type of data, which the particular diagnostic apparatus is arranged to process. The ultrasound probe 200 according to an embodiment of the present invention may transmit ultrasound image data by using different wireless communication methods according to one of the plurality of the diagnostic apparatuses 31, 32, 33, and 34, to which the probe is at one particular time connected. The functioning of the probe is adapted to establish and maintain communications according to the wireless communication type and the type of data that the diagnostic apparatus is arranged to process.

A method of operating the ultrasound probe 200 according to an embodiment of the present invention that includes determining data types that may be processed by at least one of the plurality of diagnostic apparatuses 31, 32, 33, and 34 and transmitting transmission data corresponding to the determined data types to the diagnostic apparatuses 31, 32, 33, and 34 will now be described in detail with reference to FIGS. 3 through 5 below.

Figure 3:
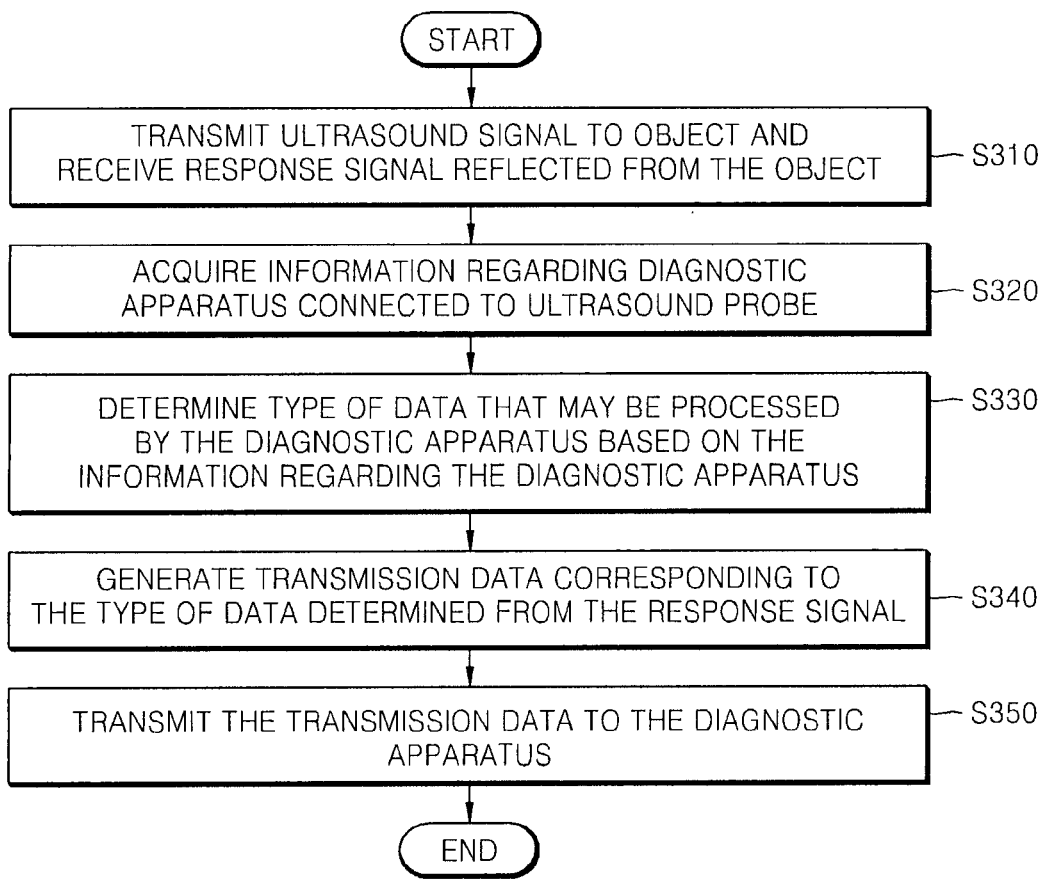
FIG. 3 is a flowchart of a method of operating an ultrasound probe according to an embodiment of the present invention.

FIG. 3 is a flowchart of a method of operating the ultrasound probe 200 according to an embodiment of the present invention.

In operation S310, the ultrasound probe 200 transmits an ultrasound signal to an object and receives a response signal reflected from the object or from within the object.

The ultrasound probe 200 may be controlled by a control signal received from a diagnostic apparatus connected to the ultrasound probe 200. The ultrasound probe 200 according to an embodiment of the present invention may be connected to any one of a plurality of diagnostic apparatuses at one time, or to more than one of the diagnostic apparatuses, while the ultrasound probe 200 may be temporarily dependent upon at least one diagnostic apparatus according to a predetermined movement of a user.

The predetermined movement of the user may include connecting a communication cable of the ultrasound probe 200 to a diagnostic apparatus, approaching or contacting the ultrasound probe 200 to the diagnostic apparatus, selecting the diagnostic apparatus that is to be connected to the ultrasound probe 200, and selecting connection to the ultrasound probe 200 through the diagnostic apparatus.

That the ultrasound probe 200 is temporarily dependent upon the diagnostic apparatus may mean that the ultrasound probe 200 and the diagnostic apparatus are paired to form a session. The "session" may mean a logical connection for communication between the diagnostic apparatus and the ultrasound probe 200. To form the session, a process of having the diagnostic apparatus and the ultrasound probe 200 recognized each other by communicating a message therebetween occurs.

In operation S320, the ultrasound probe 200 acquires information regarding the diagnostic apparatus connected to the ultrasound probe 200.

The ultrasound probe 200 may acquire the information regarding the diagnostic apparatus through the session formed therebetween. The ultrasound probe 200 may acquire the information regarding the diagnostic apparatus by exchanging the message for forming the session therebetween. Thus, unlike in FIG. 3, operation S320 may precede operation S310. Pairing or other initial communications set-up may also occur prior to transmitting and receiving the ultrasound signals of step S310.

The information regarding the diagnostic apparatus may include at least one of a type of data that may be processed by the diagnostic apparatus, a wired or wireless communication method used by the diagnostic apparatus, and an identifier of the diagnostic apparatus but is not limited thereto. The information regarding the diagnostic apparatus may include, for example, function information of the diagnostic apparatus such as quality of an ultrasound image that may be provided by the diagnostic apparatus.

As an example, the ultrasound probe 200 may receive information regarding at least one of the type of data that may be processed by the diagnostic apparatus and the preferably wireless communication method used by the diagnostic apparatus from the diagnostic apparatus connected to the ultrasound probe 200. Wireless communication between the probe 200 and the diagnostic apparatus is only preferred to be able to dispense with hindering cables, but the invention is not limited thereto, and may include wired communication methods.

For example, the ultrasound probe 200 may request the diagnostic apparatus to transmit information regarding the diagnostic apparatus. The diagnostic apparatus may transmit the information regarding the diagnostic apparatus to the ultrasound probe 200 in response to a received request. For example, the diagnostic apparatus may transmit information regarding at least one of a type of data that is to be processed by the diagnostic apparatus, a communication method that is to be used by the diagnostic apparatus, a bandwidth that is to be used by the diagnostic apparatus, and a type of a communication channel that is to be used by the diagnostic apparatus to the ultrasound probe 200. The ultrasound probe 200 may process a response signal corresponding to the information received from the diagnostic apparatus to transmit transmission data to the diagnostic apparatus.

Alternatively, the ultrasound probe 200 may receive information relating to capability of the diagnostic apparatus from the diagnostic apparatus. The ultrasound probe 200 may receive information regarding all communication methods that may be supported by the diagnostic apparatus and types of all pieces of data that may be processed by the diagnostic apparatus. The ultrasound probe 200 may select at least one communication method and the type of at least one type of data from the received information. For example, the ultrasound probe 200 may select the communication method or the type of data that allows the diagnostic apparatus to provide an ultrasound image to a user at a highest resolution or at a highest frame rate. The ultrasound probe 200 may generate transmission data based on the selected type of data and transmit the transmission data to the diagnostic apparatus by using the selected communication method.

As another example, the ultrasound probe 200 may receive only the identifier of the diagnostic apparatus from the diagnostic apparatus connected to the ultrasound probe 200. The ultrasound probe 20 may acquire the information regarding the diagnostic apparatus by searching for information regarding the diagnostic apparatus previously stored in the ultrasound probe 200 based on the received identifier.

For example, the ultrasound probe 200 may map and store at least one of a type of data that may be processed by each of a plurality of diagnostic apparatuses and a communication method used by each of the diagnostic apparatuses and an identifier of each of the diagnostic apparatuses. The ultrasound probe 200 may acquire the identifier of the diagnostic apparatus from the diagnostic apparatus and search for information corresponding to the acquired identifier to establish the type of data that the diagnostic apparatus identified by the acquired identifier thereof is configured, able or arranged to process. The ultrasound probe 200 may acquire the information regarding at least one of the type of data that may be processed by the diagnostic apparatus and the communication method used by the diagnostic apparatus based on a result of searching for the identifier and determining a stored and mapped type of data is to be used for communications with the diagnostic apparatus to which the probe is connected.

In operation S330, the ultrasound probe 200 determines the type of data that may be processed by the diagnostic apparatus based on the information regarding the diagnostic apparatus.

The diagnostic apparatus having various capabilities and characteristics may process different types of data. Thus, the ultrasound probe 200 determines a step at which the diagnostic apparatus may process data from among a series of processes of acquiring an ultrasound image from the response signal received from the object.

The ultrasound probe 200 may determine that the diagnostic apparatus may process only one type of data or that the diagnostic apparatus may process different types of data.

Essentially, steps S320 and S330 can be condensed, simplified or combined in a single step of determining at least one type of data that a diagnostic apparatus is arranged to process, which diagnostic apparatus is connected to the ultrasound probe, from a plurality of various diagnostic apparatuses, which are connectable to the ultrasound probe.

In operation S340, the ultrasound probe 200 generates transmission data corresponding to the type of data determined in operation S330 from the response signal.

The ultrasound probe 200 according to an embodiment of the present invention generates transmission data corresponding to a type of data that may be processed by the diagnostic apparatus by using a response signal. For example, the type of data may indicate at least one of: data content such as raw data which comprises pixel by pixel full detailed content, MPEG3 streams, MPEG4 streams, and the like; and/or data format for different types of communications (for instance the wireless types of communications of at least one of wireless LAN, Wi-Fi, Bluetooth, Zigbee, WFD, UWB, IrDA, BLE, NFC, Wibro, WiMAX, SWAP, WiGig, and RF communication).

One or more embodiments of the present invention provide a method of outputting data appropriate to the diagnostic apparatus by allowing the ultrasound probe 200 to recognize a signal and/or image processing process that may be performed by the diagnostic apparatus and to have the probe perform a signal and/or image processing process or selected number of steps (including zero or all) in such a process, that may not be performed by the diagnostic apparatus.

That is, the ultrasound probe 200 according to an embodiment of the present invention may selectively output intermediate data generated in an optional processing step from among a series of processes of acquiring the ultrasound image of the object from the response signal received from the object. The intermediate data generated in the processing step selected based on the information regarding the diagnostic apparatus may be the transmission data corresponding to the type of data that may be processed by the diagnostic apparatus.

For example, the ultrasound probe 200 according to an embodiment of the present invention includes basically at least one image processing unit and preferably a plurality of image processing units that process the response signal received from the object in subsequent processing steps. The ultrasound probe 200 may select an image processing mode for the image processing unit and/or the at least one image processing unit from the plurality of image processing unit, necessary for generating the transmission data corresponding to the type of data, which the diagnostic apparatus is arranged to process, which type of data is determined in operation S330. The ultrasound probe 200 may generate the transmission data from the response signal by using the selected at least one of the plurality of image processing units or a mode of image and/or signal processing to be performed by a single more versatile image processing unit. Such a more versatile image processing unit may be a programmable processor, adapted to perform different types of signal and/or image processing for example in subsequent steps or stages, depending on the determined type of data that the diagnostic apparatus is arranged to process subsequently to obtain the ultrasound inage.

In this regard, in an embodiment having a plurality of image processing units, the ultrasound probe 200 may reduce power consumption by disabling the image processing units excluding the selected at least one image processing unit. Alternatively, in an embodiment of the present disclosure having a single (signal or image) processor or other processor, which is arranged to perform several or all of a number of subsequent steps or stages to process the response signal towards the ultrasound image, not all subsequent stages need to be performed by the (image) processor or other processor to provide a readily displayable image. For example, if a diagnostic apparatus is only capable of displaying completely processed image data or ultrasound images, the probe must furnish completely processed image data to the diagnostic apparatus. However, if the diagnostic apparatus is capable of or arranged for processing the received transmission data in a form partly processed by the probe or completely unprocessed by the probe, power consumption of the probe may be reduced, by transmitting to the diagnostic apparatus completely unprocessed or partially processed transmission data, which needs further processing to arrive at image data or the ultrasound image, ready for display on a screen or the like, where such completing processing is performed by the diagnostic apparatus.

An embodiment in which the ultrasound probe 200 generates transmission data of a different type of data according to the diagnostic apparatus will be described in detail with reference to FIG. 4 later.

When one diagnostic apparatus is connected through cables, wires or wirelessly and determined to process various types of data, the ultrasound probe 200 may select one of any number of types of data that may be processed by the diagnostic apparatus and generate transmission data corresponding to the selected type of data.

The ultrasound probe 200 may determine a type of the transmission data in further consideration of a state of the ultrasound probe 200 such as remaining battery charge. In general, the ultrasound probe 200 may have a limited resource compared to the diagnostic apparatus, for example, a limited processing speed of a processor or a limited capacity of a memory. Thus, to increase the processing speed and prevent an overload of the ultrasound probe 200, the ultrasound probe 200 may generate the transmission data in a data type requiring the minimum number of processing steps in the ultrasound probe 200 from among types of data that may be processed by the diagnostic apparatus. Further processing steps to arrive at displayable image data or ultrasound image may then be performed in or by the diagnostic apparatus, thus relieving the load of the probe 200.

In operation S350, the ultrasound probe 200 transmits the transmission data to the diagnostic apparatus.

An example in which the ultrasound probe 200 transmits the transmission data to the diagnostic apparatus wirelessly will now be described. An embodiment of the present invention is not limited to the example. The ultrasound probe 200 may transmit the transmission data by wire.

To receive the transmission data from the ultrasound probe 200, diagnostic apparatuses may use different wired or wireless communication methods. Wireless communication methods used by diagnostic apparatuses may be different according to specifications or peripheral environments of diagnostic apparatuses. Alternatively, wireless communication methods used by diagnostic apparatuses may be different according to bandwidths of types of data that may be processed by diagnostic apparatuses. This is because transmittable and receivable bandwidths are different according to wireless communication methods.

Therefore, the ultrasound probe 200 may determine the wireless communication method used by the diagnostic apparatus based on the information regarding the diagnostic apparatus acquired in operation S320. The ultrasound probe 200 may transmit the transmission data to the diagnostic apparatus by using the determined wireless communication method.

For example, the ultrasound probe 200 may determine at least one of wireless LAN, Wi-Fi, Bluetooth, Zigbee, Wi-Fi Direct (WFD), UWB, infrared data association (IrDA), Bluetooth low energy (BLE), near field communication (NFC), wireless broadband Internet (Wibro), world interoperability for microwave access (WiMAX), shared wireless access protocol (SWAP), wireless gigabit allicance (WiGig), radio frequency (RF) communication, and similar communication methods as the wireless communication method used by the diagnostic apparatus.

The ultrasound probe 200 according to an embodiment of the present invention may include a plurality of communication units that may transmit the transmission data by using different communication methods. The ultrasound probe 200 may select at least one communication unit corresponding to the communication method used by the diagnostic apparatus from the communication units. For example, the ultrasound probe 200 may select at least one communication unit based on a bandwidth of the transmission data that is to be transmitted to the diagnostic apparatus. The ultrasound probe 200 may transmit the transmission data by using the selected at least one communication unit. It is noted here that available communication bandwidth can be detected either by the diagnostic apparatus or the probe and result in selection of a degree of processing starting from the response signal towards resulting images, where only a part of these processing steps may be performed in or by the probe, which would allow a best suited mode of communication, amount of data to be communicated and the like in relation to the bandwidth. Similar other factors or considerations could also be taken into account for this selection, such as types of communication channels by which a probe and a diagnostic apparatus can be connected. Consequently, in addition to a capability of the diagnostic apparatus to continue processing where the probe has stopped and transmitted intermediate results in transmission data to the diagnostic apparatus, other factors like bandwidth can also play a role in determining how far the probe is to proceed in performing a sequence of a number of processing step from the response signal to images, to allow the most suitable transmission of the transmission data and subsequent processing by the diagnostic apparatus. As a further example reference is made here to a type of communication channel, and—in wireless communication—a relation between a theoretical maximum communication speed and an actually achieved communication speed.

For all embodiments of the present disclosure, either explicitly shown and/or described or merely referred to, the probe is capable of all or many of the processing steps, which start on the response signal and progress towards displayable images. However, the probe can detect circumstances like mode of connection, bandwidth, actual transmission speeds, and processing capability of the diagnostic apparatus how many of the processing steps, that the probe is capable of, are actually to be performed up to the point of progress at which the transmission data is formed for transmission to the diagnostic apparatus. By the same token, the diagnostic apparatus may notify the probe of information, to set the level of progress that the probe should perform in a sequence of processing steps, of which the probe is capable, before transmitting the intermediate or final result, in or with the transmission data. Such information may have the form of a command from the diagnostic apparatus, which may even be input by a user, operator or physician.

The ultrasound probe 200 may use a plurality of wireless communication methods to communicate with one diagnostic apparatus. The ultrasound probe 200 may use different wireless communication methods according to characteristics of data that is to be transmitted.

That is, the ultrasound probe 200 may determine a first wireless communication method and a second wireless communication method that are used by the diagnostic apparatus based on the information regarding the diagnostic apparatus. The ultrasound probe 200 may select a first communication unit corresponding to the first wireless communication method and a second communication unit corresponding to the second wireless communication method from among the communication units. The ultrasound probe 200 may transmit the transmission data by using the first communication unit and transmit at least one of state information data of the ultrasound probe 200 and/or receive control data of the diagnostic apparatus by using the second communication unit, or the like.

The state information data of the ultrasound probe 200 may include the remaining battery charge, location information of the ultrasound probe 200, and information about whether the object is scanned by using the ultrasound probe 200. The control data of the diagnostic apparatus may include a control signal relating to an operation of controlling the ultrasound probe 200 in the diagnostic apparatus or a control signal relating to an operation of displaying the ultrasound image generated by using the transmission data received from the ultrasound probe 200 on the screen in such a manner that the ultrasound probe 200 may transceive the ultrasound signal.

Figure 4:
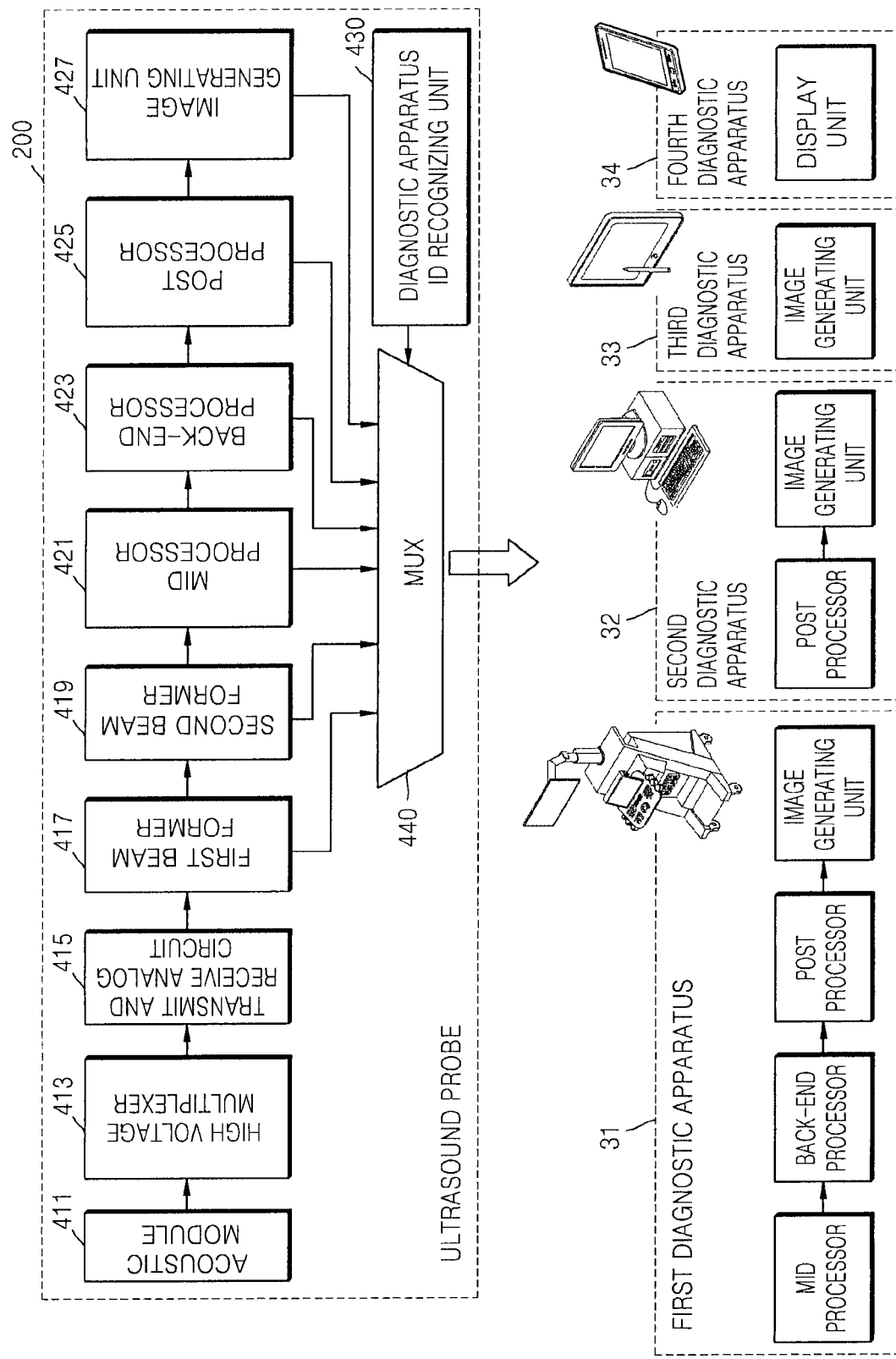
FIG. 4 is a block diagram of an ultrasound probe that generates transmission data corresponding to a type of data that may be processed by a diagnostic apparatus according to an embodiment of the present invention.

FIG. 4 is a block diagram of the ultrasound probe 200 that generates transmission data corresponding to a type of data that may be processed by a diagnostic apparatus according to an embodiment of the present invention.

Referring to FIG. 4, the ultrasound probe 200 according to an embodiment of the present invention may include a plurality of image processing units that process a response signal received from an object. However, the image processing units included in the ultrasound probe 200 according to an embodiment of the present invention are not limited to those shown in FIG. 4. The ultrasound probe 200 may include less or more image processing units than those of FIG. 4.

An acoustic module 411 receives the response signal reflected from the object. The response signal reflected from the object may be an ultrasound signal that is reflected from the object. The acoustic module 411 may include a plurality of transducers. The transducers may vibrate according to transferred electrical signals, generate ultrasound waves that are acoustic energy, process acoustic energy reflected from the object, and generate electrical signals.

A high voltage multiplexer HV mux 413 may sequentially select the transducers of the acoustic module 411. A transmit and receive T/RX analog circuit 415 separates signals acquired by processing a signal used to transmit the ultrasound signal to the object and the response signal received from the object. First and second beam formers 417 and 419 perform focusing on the response signal to determine a reflective characteristic of a tissue of a desired part of the object from the response signal. The first and second beam formers BF1 417 and BF2 419 may be an analog beam former and a digital beam former, respectively.

A mid processor 421 may perform mid processing on signals beam formed by the first and second beam formers 417 and 419. For example, the mid processor 421 may control gains of the beam formed signals. The mid processor 421 may perform phase rotation on each of a plurality of separated regions with respect to predetermined depths of the object according to dynamic frequency variations so as to compensate for frequency variations with respect to the depths of the object. The mid processor 421 may perform low band pass filtering.

A back-end processor 423 may detect envelopes of I component data and Q component data that are output from the mid processor 421. A post processor 425 may perform digital signal processing (DSP) to generate a Doppler (D) mode image and a color (C) mode image. An image generating unit 427 may generate an image that may be displayed on a screen from the processed signal.

As shown in FIG. 4, the diagnostic apparatuses 31, 32, 33, and 34 may process different types of data. That is, the various diagnostic apparatuses may in general be arranged to generate ultrasound image from any intermediate signal or image data, that may be obtained from any of the above described components 413, 415, 417, 419, 421, 423, 425. Hence these components are referred to herein as image processors (413-419, 421-427). Thus, the ultrasound probe 200 according to an embodiment of the present invention provides a method of outputting data in an appropriate form to the diagnostic apparatuses 31, 32, 33, and 34 according to a type of data that may be processed by each of the diagnostic apparatuses 31, 32, 33, and 34 or any one thereof, that is actually connected with the probe at any given time, in such a manner that the ultrasound probe 200 may be used by being connected to various diagnostic apparatuses simultaneously or at different times.

The ultrasound probe 200 may recognize an identifier (ID) of a diagnostic apparatus connected to the ultrasound probe 200 through a diagnostic apparatus ID recognizing unit 430. The ultrasound probe 200 may recognize signal processing that may be performed by the diagnostic apparatus based on the ID of the diagnostic apparatus and the ultrasound probe 200 will then perform signal processing, in particular the initial steps starting from obtaining the response signal, that may not be performed by the diagnostic apparatus, and the transmission data will then be the intermediate processing result or completely finished image data, where the diagnostic apparatus, to which the probe is connected at any one given time, is arranged to process any remaining steps or stages, necessary to arrive at displayable image data or ultrasound image for output on a display or on a screen. Load and power consumption of the probe are thus relieved.

That is, the ultrasound probe 200 may selectively output intermediate data generated in an optional processing step from among a series of subsequent processes from acquiring an ultrasound image of the object from the response signal received from the object and obtaining displayable image data. For example, the probe 200 in combination with the computer 32, the probe will generate the output of the back-end processor, where the diagnostic apparatus is capable of performing the further steps or stages that are necessary for completing the image data or ultrasound image ready for output on a screen or display, in the particular case of the computer 32 in FIG. 4, these steps or stages are those of the post processor 425 and of the image generating unit 427, which functions the probe does not need to perform, when connected with the computer 32.

For example, the first diagnostic apparatus 31 of FIG. 4 in the form of a cart like apparatus, comparable in structure with a conventional cart associated with the probe, may perform all signal processing operations except a beam forming operation. Thus, when the ultrasound probe 200 according to an embodiment of the present invention is connected to the first diagnostic apparatus 31, the ultrasound probe 200 may transmit the signal output from the second beam former 419 to the first diagnostic apparatus 31 as transmission data. In this regard, the ultrasound probe 200 may disable the mid processor 421, the back-end processor 423, the post processor 425, and the image generating unit 427 that perform processing after beam forming.

Unlike the first diagnostic apparatus 31, the fourth diagnostic apparatus 34 of FIG. 4 performs only an image display function without performing an image processing function. Thus, when the ultrasound probe 200 according to an embodiment of the present invention is connected to the fourth diagnostic apparatus 34, the ultrasound probe 200 may transmit the signal output from the image generating unit 427 to the fourth diagnostic apparatus 34 as transmission data.

The ultrasound probe 200 according to an embodiment of the present invention may transmit transmission data to diagnostic apparatuses by using a plurality of wireless communication methods. The ultrasound probe 200 may transmit transmission data to diagnostic apparatuses by using appropriate wireless communication methods according to wireless communication methods used by the diagnostic apparatuses. The ultrasound probe 200 may use a plurality of wireless communication methods to communicate with one diagnostic apparatus. The ultrasound probe 200 may use different communication methods according to a characteristic of data that is to be transmitted.

Figure 5:
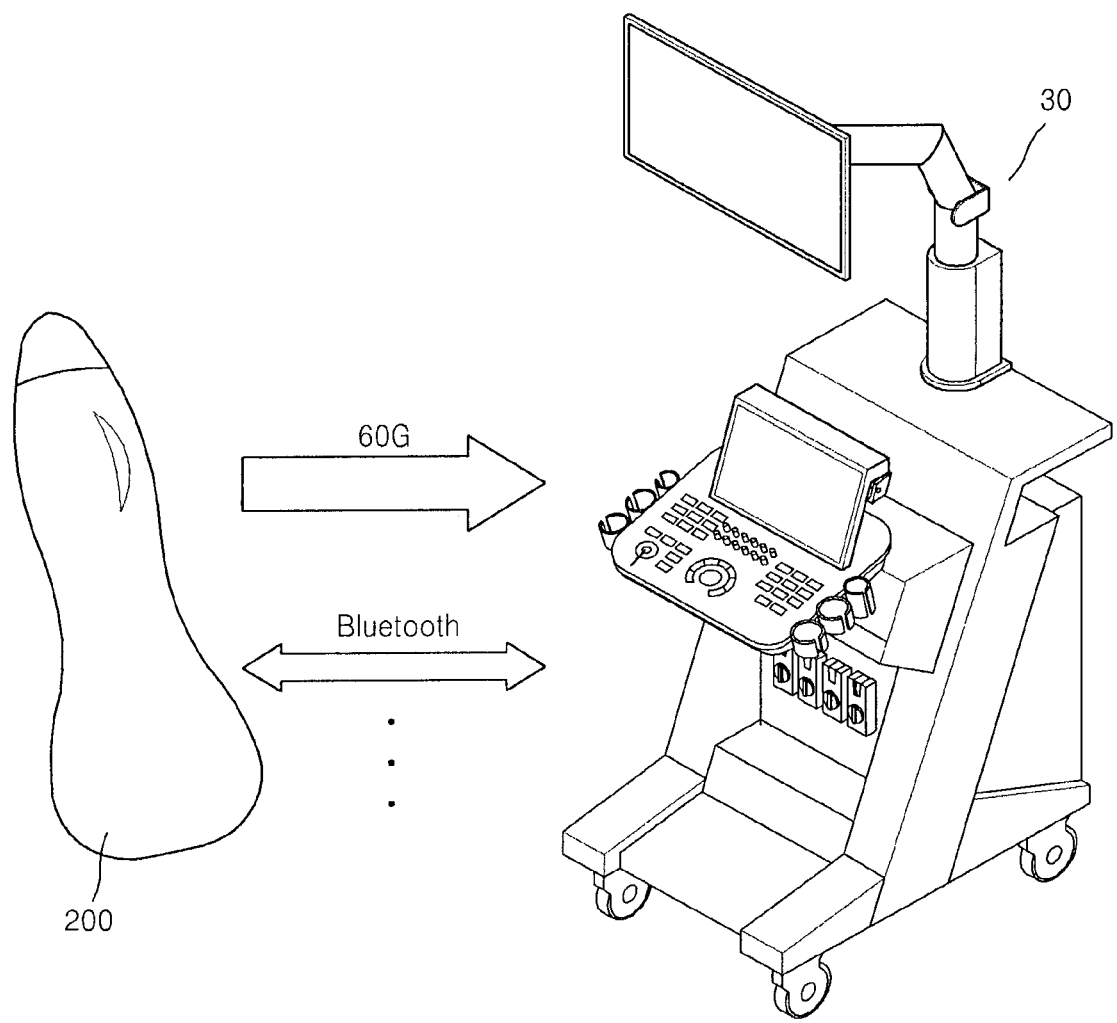
FIG. 5 is a conceptual diagram for explaining an ultrasound probe that communicates with a diagnostic apparatus by using a plurality of wireless communication methods according to an embodiment of the present invention.

FIG. 5 is a conceptual diagram for explaining the ultrasound probe 200 that communicates with a diagnostic apparatus 30 by using a plurality of wireless communication methods according to an embodiment of the present invention.

Referring to FIG. 5, the ultrasound probe 200 according to an embodiment of the present invention may transmit transmission data to the diagnostic apparatus 30 at a frequency band of 60 GHz. A plurality of transducers included in the ultrasound probe 200 convert a response signal reflected from an object into an electrical signal. A high bandwidth in several gigabit units is required to wirelessly transmit the electrical signal converted from the response signal having acoustic energy. Furthermore, when the ultrasound probe 200 transmits the transmission data to the diagnostic apparatus 30, no interference with other wireless electronic apparatuses must be generated.

Therefore, the ultrasound probe 200 according to an embodiment of the present invention may transmit the transmission data by using a wireless communication method using millimeter waves (MMW). For example, a wireless communication method following the wireless gigabit alliance (WGA) WiGig standard may be used.

The ultrasound probe 200 may transmit at least one of state information data of the ultrasound probe 200 and control data of the diagnostic apparatus 30 by using Bluetooth separately from the transmission data transmitted at the frequency band of 60 GHz.

Figure 6:
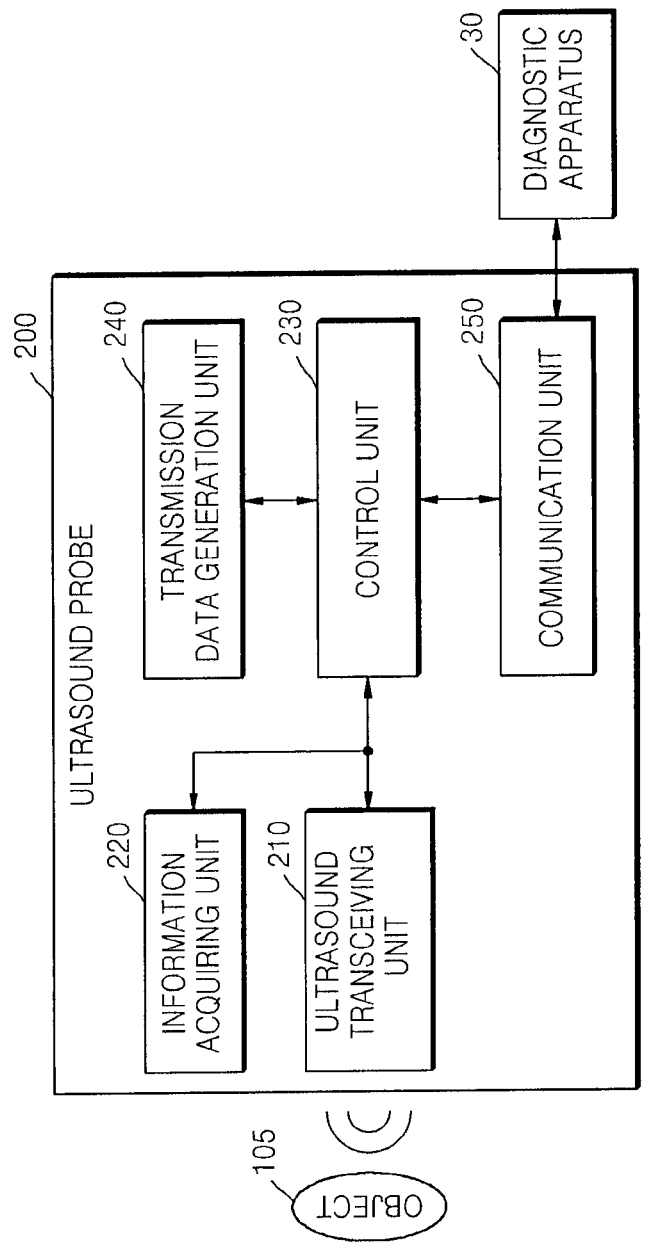
FIG. 6 is a block diagram of an ultrasound probe according to an embodiment of the present invention.
Figure 7:
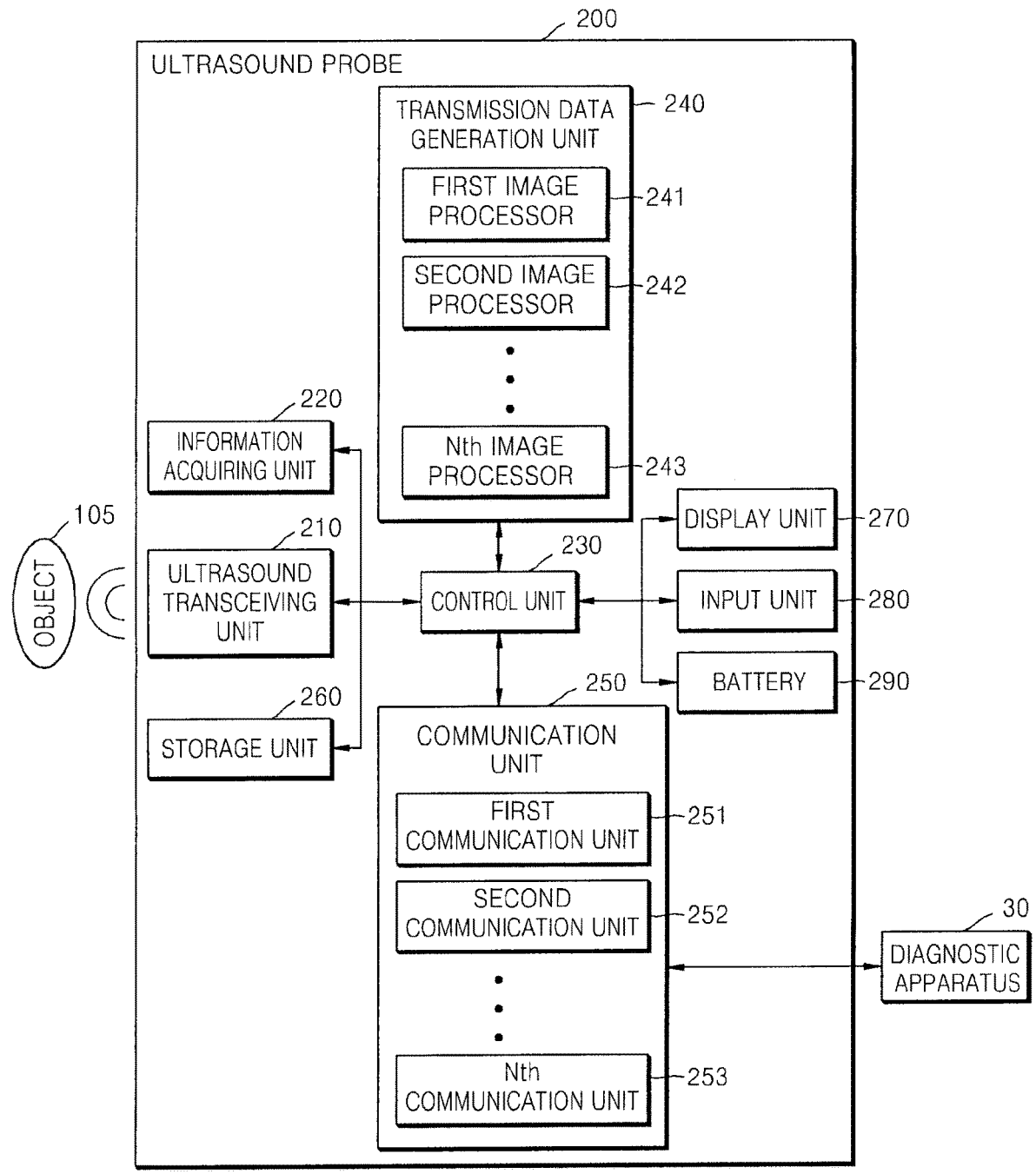
FIG. 7 is a detailed block diagram of an ultrasound probe according to another embodiment of the present invention.

FIGS. 6 and 7 are block diagrams of the ultrasound probe 200 according to an embodiment of the present invention.

Elements of the ultrasound probe 200 according to an embodiment of the present invention are configured to perform the operations of the method of operating the ultrasound probe 200 of FIG. 3. Thus, although omitted below, the descriptions of the method of operating the ultrasound probe 200 of FIG. 3 above may also apply to the ultrasound probe 200 of FIGS. 6 and 7.

Referring to FIG. 6, the ultrasound probe 200 according to an embodiment of the present invention includes an ultrasound transceiving unit 210, an information acquiring unit 220, a control unit 230, a transmission data generation unit 240, and a communication unit 250.

The ultrasound transceiving unit 210 transmits an ultrasound signal to an object 105 and receives a response signal reflected from the object 105.

The ultrasound transceiving unit 210 may generate pulses used to form transmission ultrasound according to a predetermined pulse repetition frequency (PRF). The ultrasound transceiving unit 210 may apply a delay time used to determine a transmission directionality to the pulses. Each pulse to which the delay time is applied may correspond to each of a plurality of piezoelectric vibrators included in transducers. The ultrasound transceiving unit 210 may transmit an ultrasound signal to the object 105 by applying the pulses corresponding to the piezoelectric vibrators at a time corresponding to each pulse pulse to which the delay time is applied.

The information acquiring unit 220 acquires information regarding the diagnostic apparatus 30 connected to the ultrasound probe 200. The information acquiring unit 220 may acquire at least one of a type of data that may be processed by the diagnostic apparatus 30, a wireless or wired communication method used by the diagnostic apparatus 30, available bandwidth, actual transmission speeds over a communication channel, a type of communication channel and an identifier of the diagnostic apparatus 30.

The control unit 230 determines the type of data that may be processed by the diagnostic apparatus 30 based on the information regarding the diagnostic apparatus 30. The control unit 230 may generally control operations of the ultrasound probe 200. That is, the control unit 230 may control operations between the ultrasound probe 200, the ultrasound transceiving unit 210, the information acquiring unit 220, the transmission data generation unit 240, the communication unit 250, and the diagnostic apparatus 30.

The transmission data generation unit 240 generates transmission data corresponding to the type of data determined by the control unit 230 from a response signal received from the diagnostic apparatus 30. The transmission data generation unit 240 may generate the transmission data by processing the response signal reflected from the object 105. The transmission data generation unit 240 may amplify the response signal for each channel and perform an analog-digital conversion on the amplified response signal. The transmission data generation unit 240 may apply the delay time used to determine the transmission directionality to the digitally converted response signal. The transmission data generation unit 240 may generate the transmission data by summing the response signal to which the delay time is applied.

The communication unit 250 transmits the transmission data generated by the transmission data generation unit 240 to the diagnostic apparatus 30. The communication unit 250 may perform wired or wireless communication with the diagnostic apparatus 30. The communication unit 250 may receive a control signal received from the diagnostic apparatus 30.

The communication unit 250 may be connected to a network by wire or wirelessly and communicate with an external device or a server. The communication unit 250 may transmit and receive data to and from a hospital server or other medical devices of a hospital through a picture archiving and communication system (PACS). The communication unit 250 may perform data communication according to the digital imaging and communications in medicine (DICOM) standard.

The communication unit 250 may transmit and receive data associated with a diagnosis of the object 105 such as an ultrasound image of the object 105, ultrasound data, and Doppler data over the network, and may also transmit and receive a medical image captured by another medical apparatus such as a computed tomography (CT) apparatus, a magnetic resonance imaging (MRI) apparatus, an X-ray apparatus, or the like. Furthermore, the communication unit 250 may receive a diagnosis history or treatment schedule of a patient from the server, and use the received diagnosis history or treatment schedule in diagnosing the object 105. The communication unit 250 may communicate with a mobile terminal of a doctor or a customer, in addition to the server or the medical apparatus of the hospital.

The communication unit 250 may use short distance communication such as wireless LAN, Wi-Fi, Bluetooth, Zigbee, Wi-Fi direct (WFD), ultra wideband (UWB), infrared data association (IrDA), Bluetooth low energy (BLE), near field communication (NFC), or the like, but is not limited thereto.

Wired communication technology used by the communication unit 250 may include a pair cable, a coaxial cable, an optical fiber cable, an Ethernet cable, and the like.

Mobile communication technology used by the communication unit 250 transmits and receives a wireless signal with at least one of a base station of a mobile communication network, an external terminal, and a server. In this regard, the wireless signal may include a voice signal, a video call signal, or various forms of data according to transmission and receiving of text and multimedia messages.

The diagnostic apparatus 30 may generate and display an ultrasound image by using the transmission data received from the communication unit 250. The ultrasound image displayed by the diagnostic apparatus 30 may include a gray scale ultrasound image obtained by scanning the object 105 according to an amplitude A mode, a brightness B mode, and a motion M mode as well as a Doppler image of a motion of the object 105. The Doppler image may include a blood flow Doppler image (also referred to as a color Doppler image) showing blood flow, a tissue Doppler image showing a motion of a tissue, and a spectral Doppler image showing a wave type moving speed of the object 105.

As shown in FIG. 6, the ultrasound system according to an embodiment of the present invention may include the ultrasound probe 200 and the diagnostic apparatus 30.

The ultrasound probe 200 may generate transmission data corresponding to a type of data configured to be processed by the diagnostic apparatus 30, and transmit the generated transmission data to the diagnostic apparatus 30.

The diagnostic apparatus 30 may display an ultrasound image with respect to an object on a screen by using the transmission data received from the ultrasound probe 200.

In this regard, the ultrasound probe 200 may select at least one image processing operation based on the determined type of data from among a plurality of sequential image processing operations that are to be processed to generate a displayable ultrasound image from a response signal. The ultrasound probe 200 may generate the transmission data corresponding to the determined type of data by performing the selected image processing operation. The diagnostic apparatus 30 may generate the ultrasound image from the transmission data by performing the remaining image processing operations, other than the selected image processing operation, among the plurality of image processing operations.

The ultrasound probe 200 may obtain information regarding the diagnostic apparatus 30 from the diagnostic apparatus 30. The ultrasound probe 200 may determine a type of data configured to be processed by the diagnostic apparatus 30 based on the information regarding the diagnostic apparatus 30 and determine a communication method used by the diagnostic apparatus 30. The ultrasound probe 200 may transmit the transmission data to the diagnostic apparatus 30 by using the determined communication method.

FIG. 7 is a detailed block diagram of the ultrasound probe 200 according to another embodiment of the present invention.

The ultrasound probe 200 according to an embodiment of the present invention may further include a storage unit 260, a display unit 270, an input unit 280, and a battery 290.

Referring to FIG. 7, the transmission data generating unit 240 may include a plurality of image processors 241, 242, and 243. The communication unit 250 may include a plurality of communication units 251, 252, and 253 that may use different wireless communication methods.

The control unit 230 of FIG. 7 may select at least one image processor necessary for generating transmission data corresponding to a type of data that may be processed by the diagnostic apparatus 30 from the image processors 241, 242, and 243. The control unit 230 may control the transmission data generating unit 240 to generate the transmission data by using the selected at least one image processor.

The control unit 230 may disable the image processors 241, 242, and 243 excluding the selected at least one image processor. That is, the control unit 230 may control a battery 280 to receive a power supply from the selected at least one image processor.

The control unit 230 may determine a communication method used by the diagnostic apparatus 30 based on information regarding the diagnostic apparatus 30. The control unit 230 may control the communication unit 250 to transmit the transmission data by using the determined communication method. The control unit 230 may determine at least one of wireless LAN, Wi-Fi, Bluetooth, Zigbee, WFD, UWB, IrDA, BLE, NFC, Wibro, WiMAX, SWAP, WiGig, and RF communication as the wireless communication method used by the diagnostic apparatus 30. It is noted here that in an alternative wired embodiment, the communication unit 250 may perform control of connecting the probe and the diagnostic system by using a wired communication method such as USB2.0, USB3.0, IEEE1394, SATA, LVDS, etc.

The control unit 230 may select at least one communication unit corresponding to the wireless communication method used by the diagnostic apparatus 30 from the communication units 251, 252, and 253 based on the information regarding the diagnostic apparatus 30. The control unit 230 may control the selected at least one communication unit to transmit the transmission data.

For example, a case where the diagnostic apparatus 30 may communicate with the ultrasound probe 200 by using a plurality of wireless communication methods will now be described. In this case, the control unit 230 may determine a first wireless communication method and a second wireless communication method that are used by the diagnostic apparatus 30 based on the information regarding the diagnostic apparatus 30. The control unit 230 may select the first communication unit 251 corresponding to the first wireless communication method and the second communication unit 252 corresponding to the second wireless communication method from the communication units 251, 252, and 253. The control unit 230 may control the first communication unit 251 to transmit the transmission data to the diagnostic apparatus 30 and control the second communication unit 252 to transmit at least one of state information data of the ultrasound probe 200 and control data of the diagnostic apparatus 30 to the diagnostic apparatus 30.

The storage unit 260 may map and store an identifier of each of a plurality of diagnostic apparatuses that may be connected to the ultrasound probe 200 and information regarding each of the diagnostic apparatuses. The information regarding the diagnostic apparatuses that may be stored by being mapped to the identifiers of the diagnostic apparatuses may include, for example, at least one type of data that may be processed by the diagnostic apparatuses and wireless communication methods used by the diagnostic apparatuses.

The storage unit 260 stores various types of information processed by the ultrasound probe 200. For example, the storage unit 260 may store medical data associated with a diagnosis of the object 105 such as input and output ultrasound data, and an ultrasound image, and may also store an algorithm or a program performed in the ultrasound probe 200.

The storage unit 260 may be configured as various types of storage media such as flash memory, hard disk, electrically erasable programmable read-only memory (EE- PROM), etc. The ultrasound probe 200 may operate web storage or a cloud server that performs a storage function of the storage unit 260 on the web.

The display unit 270 may display various types of information processed by the ultrasound probe 200 on a screen. Alternatively, the display unit 270 may display a user interface (UI) or a graphic user interface (GUI) associated with a function setting of the ultrasound probe 200.

The input unit 280 is used to receive an input of data for controlling the ultrasound probe 200. The input unit 280 may receive an input of selecting a diagnostic apparatus that is to be connected to the ultrasound probe 200 from a plurality of diagnostic apparatuses. The input unit 270 may include a hardware element such as a key pad, a mouse, a touch panel, a touch screen, a trackball, and a jog switch but is not limited thereto. The input unit 270 may further include various input units such as an electrocardiogram (ECG) measurement module, a respiration measurement module, a voice recognition sensor, a gesture recognition sensor, a finger print recognition sensor, an iris recognition sensor, a depth sensor, a distance sensor, and the like. An operator, user or physician may thereby input specific commands to the probe from the diagnostic apparatus, including active commands with respect to the mode of communication and/or intermediate results of processing steps which up to an indicated commanded level should be performed by the probe, and sent in, with or by the transmission data from the probe to the diagnostic apparatus for further processing thereof towards an end result in the form of displayable images, which can be visualised on the diagnostic apparatus or an associated display device.

The battery 290 may be included in the ultrasound probe 200 and may supply power necessary for operating the ultrasound probe 200.

The ultrasound transceiving unit 210, the information acquiring unit 220, the control unit 230, the transmission data generation unit 240, the communication unit 250, the storage unit 260, the display unit 270, the input unit 280, and the battery 290 may wholly or partly operate by using a software module but are not limited thereto, and may partly operate by using hardware. At least one of the information acquiring unit 220 and the transmission data generation unit 240 may be included in the control unit 230 but is not limited thereto.

In addition, other embodiments of the present invention can also be implemented through computer readable code/instructions in/on a medium, e.g., a computer readable medium, to control at least one processing element to implement any above described embodiment. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more embodiments of the present invention. The media may also be a distributed network, so that the computer readable code is stored/transferred and executed in a distributed fashion. Furthermore, the processing element could include a processor or a computer processor, and processing elements may be distributed and/or included in a single device.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

The invention claimed is:

1. An ultrasound probe comprising:
an ultrasound transceiver configured to transmit an ultrasound signal to or into an object, and obtain response signal data corresponding to a response signal reflected from the object or from within the object;
a communicator configured to communicate with a diagnostic apparatus;
an image processor; and
a controller configured to:
determine at least one first step that the diagnostic apparatus is capable of processing from among all steps necessary to arrive at displayable image data based on an identifier of the diagnostic apparatus,
control the image processor to partially process the response signal data by processing at least one second step other than the determined at least one first step among the all steps, and
control the communicator to transmit the partially processed response signal data to the diagnostic apparatus, such that a processor of the diagnostic apparatus is configured to process the at least one first step based on the partially processed response signal data.

2. The ultrasound probe of claim 1, wherein the controller is further configured to control the communicator to transmit non processed response signal data to the diagnostic apparatus.

3. The ultrasound probe of claim 1, wherein the controller is further configured to determine a wireless communication method that the diagnostic apparatus is configured to communicate with, and control the communicator to transmit data via the determined wireless communication method.

4. The ultrasound probe of claim 1, further comprising a storage for storing identifiers of a plurality of diagnostic apparatuses that are communicatively connectable to the ultrasound probe, wherein the storage includes a mapping of the stored identifiers with respect to at least one type of data that each of the plurality of diagnostic apparatuses is configured to process.

5. The ultrasound probe of claim 1, wherein the ultrasound probe comprises a plurality of communicators, and each communicator is configured to transmit data by a different method, and
wherein the controller is further configured to:
determine a first communication method and a second communication method that are used by the diagnostic apparatus,
select a first communicator corresponding to the first communication method and a second communicator corresponding to the second communication method from the plurality of communicators, and
control the first communicator to transmit the partially processed response signal data to the diagnostic apparatus and control the second communicator to transmit at least one of state information data of the ultrasound probe and control data of the diagnostic apparatus to the diagnostic apparatus.

6. The ultrasound probe of claim 1, wherein the ultrasound probe comprises a battery, and the controller is configured to determine a remaining battery charge, and wherein the controller is further configured to control the image processor to generate transmission data based on the remaining battery charge.

7. The ultrasound probe of claim 1, wherein the controller is further configured to:

determine a size of a communication bandwidth between the diagnostic apparatus and the ultrasound probe; and control the image processor to partially process the response signal data in consideration of the size of the communication bandwidth, wherein an amount of partial processing done by the image processor is inversely proportional to the size of the communication bandwidth.

8. An ultrasound system comprising:

a diagnostic apparatus including a processor and a display for displaying an ultrasound image; and an ultrasound probe, the ultrasound probe further comprising:

an ultrasound transceiver configured to transmit an ultrasound signal to or into an object and obtain response signal data corresponding to a response signal reflected from the object or from within the object;

a communicator configured to communicate with the diagnostic apparatus;

an image processor; and a controller configured to:

determine at least one first step that the diagnostic apparatus is capable of processing from among all steps necessary to arrive at displayable image data, based on an identifier of the diagnostic apparatus, control the image processor to partially process the response signal data by processing at least one second step other than the determined at least one first step among the all steps, and control the communicator to transmit the partially processed response signal data to the diagnostic apparatus, such that a processor of the diagnostic apparatus is configured to process the at least one first step based on the partially processed response signal data.

9. The ultrasound system of claim 8, wherein the controller is further configured to control the communicator to transmit non processed response signal data to the diagnostic apparatus.

10. The ultrasound system of claim 8, wherein the controller is further configured to determine a wireless communication method that the diagnostic apparatus is configured to communicate with, and control the communicator to transmit data via the determined wireless communication method.

11. The ultrasound system of claim 8, wherein the ultrasound probe further comprises a storage for storing identifiers of a plurality of diagnostic apparatuses that are communicatively connectable to the ultrasound probe, wherein the storage includes a mapping of the stored identifiers with respect to at least one type of data that each of the plurality of diagnostic apparatuses is configured to process.

12. The ultrasound system of claim 8, wherein the ultrasound probe comprises a plurality of communicators, and each communicator is configured to transmit data by a different method, and wherein the controller is further configured to:

determine a first communication method and a second communication method that are used by the diagnostic apparatus, select a first communicator corresponding to the first communication method and a second communicator corresponding to the second communication method from the plurality of communicators, and control the first communicator to transmit the partially processed response signal data to the diagnostic apparatus and control the second communicator to transmit at least one of state information data of the ultrasound probe and control data of the diagnostic apparatus to the diagnostic apparatus.

13. The ultrasound system of claim 8, wherein the ultrasound probe comprises a battery, and the controller is configured to determine a remaining battery charge, and Wherein the controller is further configured to control the image processor to generate transmission data based on the remaining battery charge.

14. The ultrasound system of claim 8, wherein the diagnostic apparatus comprises a plurality of processors.

* * * * *